United States Patent
Kazuno

(10) Patent No.: US 7,834,770 B2
(45) Date of Patent: Nov. 16, 2010

(54) BED APPARATUS HAVING MOVABLE BEDBOARD

(75) Inventor: Hiroki Kazuno, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 322 days.

(21) Appl. No.: 12/071,054

(22) Filed: Feb. 14, 2008

(65) Prior Publication Data

US 2008/0204254 A1  Aug. 28, 2008

(30) Foreign Application Priority Data

Feb. 27, 2007  (JP) .............................. 2007-048168

(51) Int. Cl.
*G08B 23/00* (2006.01)
(52) U.S. Cl. ....................... 340/573.4; 5/618
(58) Field of Classification Search .............. 340/573.4; 5/617–619; 177/45, 144, 199
See application file for complete search history.

(56) References Cited

U.S. PATENT DOCUMENTS

| | | | | |
|---|---|---|---|---|
| 5,276,432 | A * | 1/1994 | Travis | 340/573.4 |
| 6,336,235 | B1 * | 1/2002 | Ruehl | 5/618 |
| 7,165,277 | B2 * | 1/2007 | Taguchi et al. | 5/618 |
| 7,253,366 | B2 * | 8/2007 | Bhai | 177/144 |
| 2003/0090383 | A1 * | 5/2003 | Conway | 340/573.4 |
| 2009/0260158 | A1 * | 10/2009 | Kazuno et al. | 340/573.4 |

FOREIGN PATENT DOCUMENTS

| | | |
|---|---|---|
| JP | 02-280733 | 11/1990 |
| JP | 3093745 | 7/2000 |
| JP | 3322632 | 6/2002 |

OTHER PUBLICATIONS

Barbenel et al.; "Monitoring the mobility of patients in bed", Medical & Biological Engineering & Computing, Sep. 1985, pp. 466-468.

* cited by examiner

*Primary Examiner*—John A Tweel, Jr.
(74) *Attorney, Agent, or Firm*—McGinn Intellectual Property Law Group, PLLC

(57) ABSTRACT

A body weight threshold determination unit determines that the body weight of a user on a bed is at a body weight threshold or higher, and a center-of-gravity position area determination unit determines that the center-of-gravity position thereof has moved to an abnormal position (monitored area). In such a case, the bed user is detected to be in an abnormal position when a body weight center-of-gravity position monitoring unit detects that such a state has continued for a prescribed length of time or longer. When a back-raising operation has been carried out, a movable bedboard determination unit inputs the movable bedboard information, and a monitored area adjustment unit adjusts the monitored area. The monitored area is thereby constantly set to a suitable area in accordance with the state of the movable bedboard. In this manner, the combined information of the body weight information and center-of-gravity position information of the user is determined, whereby the movement of the user can be more accurately monitored with fewer misdetections, high detection accuracy, and high reliability in an electric bed having a movable bedboard.

20 Claims, 4 Drawing Sheets

(a)   (b)

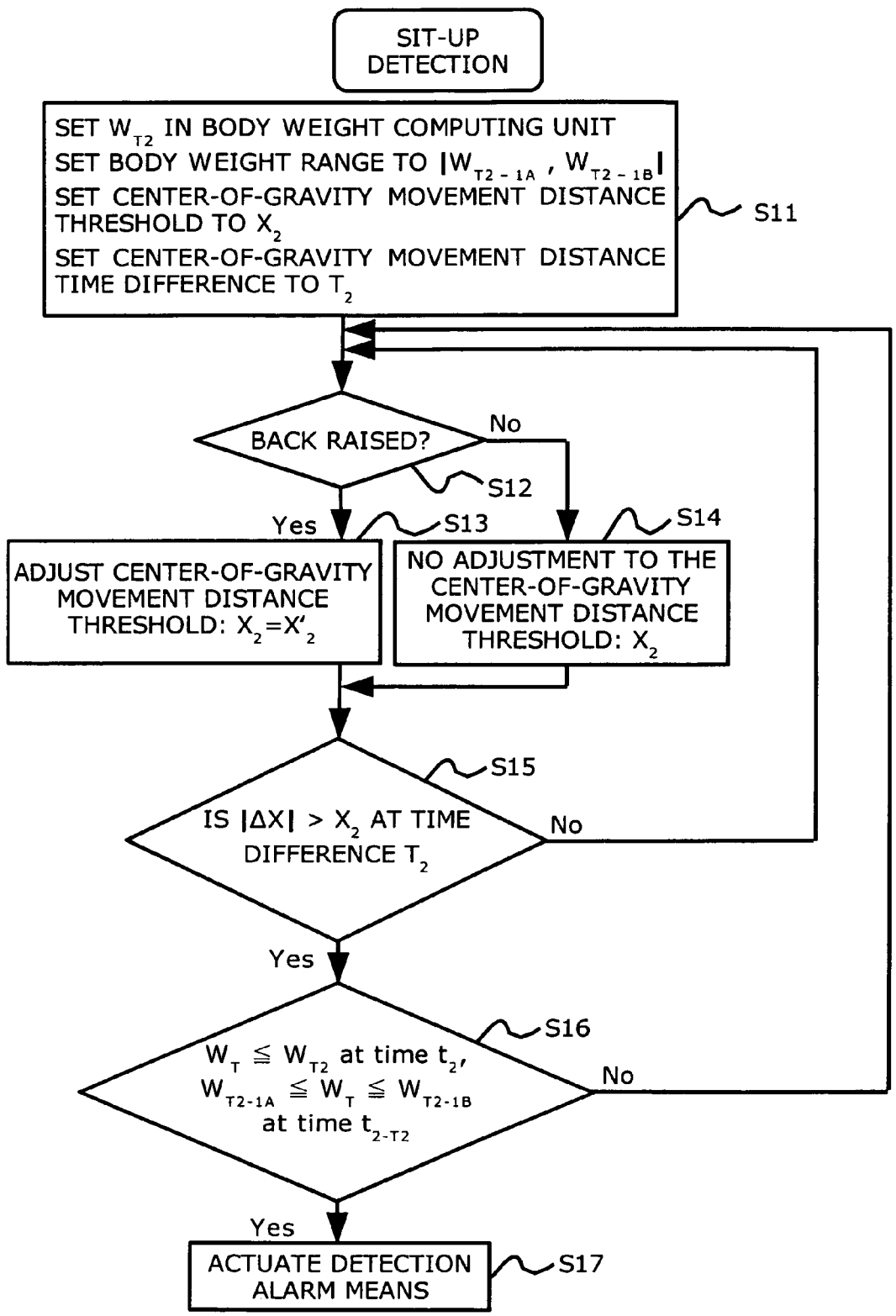

BED APPARATUS HAVING MOVABLE BEDBOARD

BACKGROUND OF THE INVENTION

1. Field of the Invention

The present invention relates to a bed apparatus provided with a bed-departure prediction and detection system for determining bed-departure/bed-presence of elderly persons suffering from dementia, patients that have recently undergone surgery, or other persons, and for predicting bed-departure on the basis of the movement of a user on the bed, and particularly relates to a bed apparatus having a movable bedboard that performs a back-raising movement and/or a knee-raising movement.

2. Description of the Related Art

In recent years, wandering of elderly persons suffering from dementia and accidents involving stumbling and falling in the vicinity of the bed have become a social problem, and a solution to this problem is needed. There are high expectations that a quicker response can be achieved during an abnormal situation by monitoring the on-bed movements of elderly persons, patients that have recently undergone surgery, or other users who are bedridden over a long period of time, by using the load information of the bed.

The art disclosed in Japanese Laid-Open Patent Application No. 2-280733 merely uses load information to determine whether a user is still on the bed or has left the bed, and cannot monitor the movement of the user on the bed.

The arts disclosed in Japanese Patent Nos. 3093745 and 3322632, U.S. Pat. No. 5,276,432, and J. C. Barbenel et al., Monitoring the mobility of patients in bed, Medical & Biological Engineering & Computing, pp. 466-468 (September 1985) solve this problem by calculating the center of gravity from the weight information of four points on the bed, and uses the center-of-gravity position information to monitor the movement of a user in bed.

However, in Japanese Patent Nos. 3093745 and 3322632, and U.S. Pat. No. 5,276,432, even though the user can be determined to be at the edge of the bed, for example, by monitoring only information related to the center-of-gravity position of the user on the bed, it cannot be determined whether the user is at the edge of the bed due to turning over in bed or moving in another manner, whether the user is at the edge of the bed in an attempt to leave the bed, or whether the variations in the center-of-gravity position are due to an item being placed on the bed section in which the user is sleeping, or another non-user person leaning or sitting on the bed section. Also, there is a problem in that distinction cannot be made from a sit-up movement, and errant determinations may occur when the center of gravity has changed due to the railing or other accessory items being removed.

The art disclosed in J. C. Barbenel et al. is one in which the load of four bed legs is measured by load cells, and the body weight of the patient on a bed is measured in order to monitor the movement of a patient on the bed. The center of gravity on the bed is computed from the difference in the load measurement values of the bed legs, and the movement distance of the center of gravity is computed. Also disclosed is an art in which the state of the patient is determined from the number of movements of the patient on the bed.

However, in the art disclosed in J. C. Barbenel et al., there is a problem in that the movement of the user on the bed cannot be determined to be movement of the center of gravity that is caused by an item being placed on the bed section in which the user is sleeping, or another non-user person leaning or sitting on the bed section, because the movement of the user on the bed is measured by using only the movement distance of the center of gravity on the bed, and such a situation leads to errant determinations.

The prior arts described above have a problem in that a back bottom (back bedboard), a hip bottom (hip bedboard), and a knee bottom (knee bedboard), for example, are provided to the bed frame, the hip bottom is fixed to the frame, and the back bottom pivots about the center of the end section of the hip bottom side. False alarms are thereby generated and detection accuracy is reduced because the center of gravity varies when the back has been raised in a bed apparatus that is provided with a movable bedboard in which the back bottom is electrically raised. This is the same as in electric beds in which the knee bottom lifts the position of the knee when the knee bottom pivots about the center of the end section of the hip bottom side.

In this manner, there is a problem in that the center-of-gravity position of the bed user varies due to the back-raising movement and knee-raising movement in a conventional electric bed having a movable bedboard, and false alarms are generated indicating that the user has moved to a edge-sitting position and the detection accuracy of whether the bed user is at the edge of the bed or not is reduced regardless of whether the bed user has moved on the bed.

SUMMARY OF THE INVENTION

An object of the present invention is to provide a bed apparatus having a movable bedboard that is provided with a bed-departure prediction and detection system in which the movement of a user can be more accurately monitored by determining information that includes a combination of the body weight information and center-of-gravity position information of the user, and the movement of a user can be monitored with high reliability with few detection errors and high detection accuracy, even in an electric bed having a movable bedboard.

The bed apparatus having a movable bedboard according to a first aspect of the present invention comprises load measuring unit for detecting the load of a bed section and generating a load signal; body weight computing unit for computing the weight of a user positioned on the bed section on the basis of the load signal; body weight threshold determination unit for determining whether the body weight is equal to or greater than a prescribed threshold; center-of-gravity position computing unit for computing a center-of-gravity position of the user on the basis of the load signal; center-of-gravity position area determination unit for determining whether the center-of-gravity position is in a monitored area of the bed section; body weight center-of-gravity position monitoring unit for monitoring the time in which the body weight is equal to or greater than a prescribed threshold and the center-of-gravity position is in the monitored area, on the basis of the determination result of the body weight threshold determination unit and center-of-gravity position area determination unit; movable bedboard information recognition unit for inputting a state of a movable bedboard of the bed; and monitored area adjustment unit for adjusting the monitored area on the basis of the movable bedboard information of the movable bedboard information recognition unit, wherein the monitored area adjustment unit adjusts the monitored area and sets the adjusted monitored area in the center-of-gravity position area determination unit, and the center-of-gravity position monitoring unit detects the state of the user when the monitored time is continuous and has exceeded a prescribed time, in the case that the movable bedboard information that has been inputted to the movable bedboard information recognition unit has been adjusted.

The center of gravity of the user moves on the bed when the user moves on the bed. At this point, the body weight center-of-gravity position monitoring unit detects that the user is in a monitored area (e.g., abnormal position) and that there is danger when the body weight of the user is at or above a prescribed threshold and the center-of-gravity position is in the monitored area. In other words, it is determined that the state of the user is different than a normal sleeping posture because the user is in the monitored area, and since the body weight of the user is at a prescribed threshold or higher, there is a possibility that the user or a part of the body of the user is on the bed, the user is leaning on the railing, or the user has fallen from the bed and a part of the body of the user is leaning on a portion of the bed. The body weight center-of-gravity position monitoring unit monitors the time in which such a state exists, and when such a state has continued and exceeded a prescribed time, it is determined that the user is unmistakably in a dangerous state rather than a state in which the center of gravity has entered the monitored area when the user temporarily turned over in bed or the like. In other words, the state of the user is detected to be dangerous (in a state in which the nurse or other staff should be warned).

When the movable bedboard moves, e.g., a back-raising action is carried out, the center-of-gravity position moves even if the bed user has not moved on the bed. For this reason, the center-of-gravity position of the user enters the monitored area and the state of the user is errantly detected to be dangerous after the back-raising action has been completed, even when the bed user has not moved. The situation is the same for when a knee-raising action is carried out in an electric bed having a movable bedboard, and it is highly likely that false alarm indicating danger will be generated even when the bed user has not moved. Conversely, there are cases in which the bed user has moved to a sitting position at the edge while remaining recumbent, or other dangerous cases in which the center-of-gravity position of the user will depart from the monitored area due to a back-raising action or another bedboard movement, and such cases cannot be detected. In response to this situation, in the present invention, the monitored area adjustment unit adjusts the monitored area on the basis of the movable bedboard information inputted to the movable bedboard information recognition unit, and sets the adjusted monitored area in the center-of-gravity position area determination unit when the state of the bed has been adjusted by the movable bedboard action, because the state of the back bottom or other movable bedboard of the bed is inputted to the movable bedboard information recognition unit. For this reason, the monitored area is constantly set in a suitable area in accordance with the state of the movable bedboard.

The bed apparatus having a movable bedboard according to a second aspect of the present invention comprises load measuring unit for detecting the load of a bed section and generating a load signal; body weight computing unit for computing the weight of a user positioned on the bed section on the basis of the load signal; body weight range determination unit for determining whether the body weight is within a prescribed body weight range; center-of-gravity position computing unit for computing a center-of-gravity position of the user on the basis of the load signal; center-of-gravity position area determination unit for determining whether the center-of-gravity position is in a monitored area of the bed section; body weight center-of-gravity position monitoring unit for monitoring the time in which the body weight is within a prescribed range and the center-of-gravity position is in the monitored area, on the basis of the determination result of the body weight range determination unit and center-of-gravity position area determination unit; movable bedboard information recognition unit for inputting a state of a movable bedboard of the bed; and monitored area adjustment unit for adjusting the monitored area on the basis of the movable bedboard information of the movable bedboard information recognition unit, wherein the monitored area adjustment unit adjusts the monitored area and sets the adjusted monitored area in the center-of-gravity position area determination unit, and the center-of-gravity position monitoring unit detects the state of the user when the monitored time is continuous and has exceeded a prescribed time, in the case that the movable bedboard information that has been inputted to the movable bedboard information recognition unit has been adjusted.

In the first aspect described above, when the body weight of the user on the bed that has been calculated by the body weight computing unit is determined by the body weight threshold determination unit to be at a prescribed threshold or higher, the state in which the user is, e.g., in an abnormal position of the bed section is detected when other conditions are satisfied. In contrast, in the second aspect of the present invention, the state of the user is detected when the body weight range determination unit determines whether the body weight is within a prescribed range and the body weight is indeed within the prescribed range, and when the center-of-gravity position area determination unit also determines that the center-of-gravity position is in the monitored area and this state has continued for a prescribed length of time. In the same manner as the first aspect, the second aspect also uses the body weight detection value of the user on the bed to detect that the bed user is in an abnormal position. However, an upper limit may also be used to make the determination in addition to a lower limit.

This may result in misdetections in that the result of computing the center-of-gravity position no longer indicates the position of the bed user when a caregiver or the like places an object on the bed. However, as described in the second aspect, the upper limit value is set to the body weight detection value, whereby the bed user is not detected to be in an abnormal position even if the center-of-gravity position has entered the monitored area. This is because the body weight detection value exceeds the upper limit in cases such as those in which an object is placed on the bed. Misdetections can thereby be avoided. In the second aspect, there are provided movable bedboard information recognition unit for inputting the state of the movable bedboard of a bed, and monitored area adjustment unit for adjusting the monitored area on the basis of the movable bedboard information of the movable bedboard information recognition unit. Therefore, misdetections and reduction of detection accuracy can be prevented because the monitored area is constantly set in an appropriate manner even if the state of the movable bedboard of the bed changes.

In the case of the first and second aspects, the monitored area is an abnormal position of the bed section, for example, and shows that the state of the user is in an unnatural state or an unnatural position.

The bed apparatus having a movable bedboard according to a third aspect of the present invention comprises load measuring unit for detecting the load of a bed section and generating a load signal; body weight computing unit for computing the weight of a user positioned on the bed section on the basis of the load signal; body weight threshold determination unit for determining whether the body weight is equal to or less than the body weight threshold; center-of-gravity position computing unit for computing a center-of-gravity position of the user on the basis of the load signal; center-of-gravity movement distance computing unit for computing, based on the computation result of the center-of-gravity position, the center-of-gravity movement distance of the center-of-gravity position; center-of-gravity movement distance threshold determination unit for determining whether the movement distance of the center-of-gravity position has exceeded a center-of-gravity movement distance threshold; movable bedboard information recognition unit for inputting the state of a movable bedboard of a bed; and threshold adjustment unit for adjusting the center-of-gravity movement distance threshold on the basis of the movable bedboard information of the movable bedboard information recognition unit, wherein the state of the user is detected when the threshold adjustment unit adjusts the center-of-gravity movement distance threshold and sets the adjusted center-of-gravity movement distance threshold in the center-of-gravity movement distance threshold determination unit, the center-of-gravity movement distance threshold determination unit determines that the movement distance of the center-of-gravity position has exceeded the center-of-gravity movement distance threshold, and the body weight threshold determination unit determines that the body weight is equal to or less than the body weight threshold, in the case that the movable bedboard information that has been inputted to the movable bedboard information recognition unit has been adjusted.

The bed apparatus having a movable bedboard according to a fourth aspect of the present invention comprises load measuring unit for detecting the load of a bed section and generating a load signal; body weight computing unit for computing the weight of a user positioned on the bed section on the basis of the load signal; body weight range determination unit for determining whether the body weight is within a prescribed range; center-of-gravity position computing unit for computing a center-of-gravity position of the user on the basis of the load signal; center-of-gravity movement distance computing unit for computing, based on the computation result of the center-of-gravity position, the center-of-gravity movement distance of the center-of-gravity position; center-of-gravity movement distance threshold determination unit for determining whether the movement distance of the center-of-gravity position has exceeded a center-of-gravity movement distance threshold; movable bedboard information recognition unit for inputting the state of a movable bedboard of a bed; and threshold adjustment unit for adjusting the center-of-gravity movement distance threshold on the basis of the movable bedboard information of the movable bedboard information recognition unit, wherein the state of the user is detected when the threshold adjustment unit adjusts the center-of-gravity movement distance threshold and sets the adjusted center-of-gravity movement distance threshold in the center-of-gravity movement distance threshold determination unit, the center-of-gravity movement distance threshold determination unit determines that the movement distance of the center-of-gravity position has exceeded the center-of-gravity movement distance threshold, and the body weight threshold determination unit determines that the body weight is within the prescribed range, in the case that the movable bedboard information that has been inputted to the movable bedboard information recognition unit has been adjusted.

The center of gravity of the user moves from the head side to the foot side in the lengthwise direction of the bed section when the user makes a sit-up action on the bed. The bed user is essentially detected to have sat up on the bed when the center-of-gravity movement distance threshold determination unit determines that the movement distance of the center-of-gravity position has exceeded a center-of-gravity movement distance threshold. However, the center-of-gravity position moves even when a heavy object is placed on the bed. In view of this, and in order to prevent misdetections of sitting up due to such an external disturbance, a state is detected to be a sit-up action when the body weight measurement value is determined to be at the body weight threshold or less in a case in which the movement distance of the center-of-gravity position has exceeded the center-of-gravity movement distance threshold in the third aspect of the present invention. In the fourth aspect of the present invention, consideration is given to a user lying on a bed, wherein the user body weight is used as a reference, and the vicinity thereof is used as a prescribed weight range. When the center-of-gravity movement has exceeded the center-of-gravity movement distance threshold, such a situation is detected to be a sit-up action because the weight on the bed is within the prescribed range when only the upper body has been raised on the bed. However, when the user rotates his body at the same time as raising his upper body and places his feet on the floor, the weight on the bed is reduced because the feet are on the floor and the body weight measured value departs from the prescribed body weight range. Therefore, in this case, getting up is not detected even when the center of gravity has moved. In this manner, in the third or fourth aspects of the present invention, it is presumed that the body weight detection value is a prescribed value (body weight threshold) or less, or is within a prescribed body weight range, and when the movement distance of the center-of-gravity position has exceeded a center-of-gravity movement distance threshold, such a situation is detected as the action of getting up.

In the present invention, there are provided movable bedboard information recognition unit for inputting the state of the movable bedboard of a bed, and threshold adjustment unit for adjusting the center-of-gravity movement distance threshold on the basis of the movable bedboard information of the movable bedboard information recognition unit. Therefore, the center-of-gravity movement distance threshold can be constantly set at a suitable level even if the state of the movable bedboard of the bed changes, and misdetections and reduced detection accuracy can be prevented. In other words, in the case that the bedboard is horizontal, the center-of-gravity position movement distance when the user is raised up is different than the center-of-gravity position movement distance when the bedboard is raised as during a back-raising operation, i.e., when the upper body of the bed user is inclined and raised from such a position. Therefore, the center-of-gravity position movement distance threshold during a back-raising operation must be reduced in comparison with when the bed section is horizontal. The present invention can prevent misdetections and assure high detection accuracy because such adjustment is carried out by the movable bedboard information recognition unit and the threshold adjustment unit.

The bed apparatus having a movable bedboard of a fifth aspect of the present invention comprises load measuring unit for detecting the load of a bed section and generating a load signal; body weight computing unit for computing the weight of a user positioned on the bed section on the basis of the load signal; first body weight range determination unit for determining whether the body weight is within the range of a first value range; second body weight range determination unit for determining whether the body weight is within the range of a second value range; center-of-gravity position computing unit for computing a center-of-gravity position of the user on the basis of the load signal; center-of-gravity movement distance computing unit for computing, based on the computation result of the center-of-gravity position, the movement distance of the center-of-gravity position; center-of-gravity movement distance threshold determination unit for determining whether the movement distance of the center-of-gravity position has exceeded a center-of-gravity movement distance threshold; movable bedboard information recognition unit for inputting the state of a movable bedboard of a bed; and threshold adjustment unit for adjusting the center-of-gravity movement distance threshold on the basis of the movable bedboard information of the movable bedboard information recognition unit, wherein in a case in which the movable bedboard information that has been inputted to the movable bedboard information recognition unit has been adjusted, the state of the user is detected when the threshold adjustment unit adjusts the center-of-gravity movement distance threshold and sets the adjusted center-of-gravity movement distance threshold in the center-of-gravity movement distance threshold determination unit, and the center-of-gravity movement distance threshold determination unit determines that the movement distance of the center-of-gravity position has exceeded the center-of-gravity movement distance threshold, whereupon the first body weight range determination unit determines that the body weight is within the range of the first value range before the movement distance of the center-of-gravity position exceeds the center-of-gravity position movement distance threshold, and the second body weight range determination unit determines that the body weight is within the range of the second value range when the movement distance of the center-of-gravity position has exceeded the center-of-gravity position movement distance threshold or thereafter.

In the fifth aspect of the present invention, first body weight range determination unit determines that the body weight detection value is within the range of a first value range, and the second body weight range determination unit determines that the body weight detection value is within the range of a second value range. When the center-of-gravity movement distance threshold determination unit has determined that the movement distance of the center-of-gravity position has exceeded the center-of-gravity movement distance threshold, it is determined, e.g., that the bed user has sat up on the bed because the center-of-gravity position moves in accompaniment with a sit-up action. When such a determination is made in the present invention, the body weight detection value must be within the first value range prior to the movement distance of the center-of-gravity position exceeding the center-of-gravity movement distance threshold, and the body weight detection value must be within the second value range when the movement distance of the center-of-gravity position has exceeded the center-of-gravity movement distance threshold or thereafter. The first value range is used to determine the state prior to a sit-up action, and the second value range is used to determine the state after a sit-up action. The first value range determines that the user is unmistakably on the bed, and the first value range is therefore set to a value range that is in the vicinity of the body weight of the user. The second value range is set to be a relatively wide range because it is possible that the user is on the bed, the user may have lowered his feet and is sitting on the edge of the bed. It is also possible to consider setting the second value range to be a value range that is in the vicinity of the body weight in the same manner as the first value range. However, the body weight measurement value is considerably reduced when the bed user is sitting on the side of the bed with his feet lowered to the floor. For this reason, the lower limit of the second value range is less than the lower limit of the first value range. On the other hand, in an extreme case, the center of gravity may move to a value that is equal to or greater than the center-of-gravity movement distance threshold when the weight on the bed rapidly decreases as the user sits up with great force from the bed or jumps down from the bed. Such an action is not actually a sit-up action, but may still be errantly detected as a sit-up action. In view of such a situation, the second value range must be provided with a lower limit in order to prevent such misdetections.

In the fifth aspect of the present invention, there are provided movable bedboard information recognition unit for inputting the state of the movable bedboard of a bed, and threshold adjustment unit for adjusting the center-of-gravity movement distance threshold on the basis of the movable bedboard information of the movable bedboard information recognition unit. Therefore, the center-of-gravity movement distance threshold is constantly set to a suitable level even if the state of the movable bedboard varies due to a back-raising operation or the like because the threshold adjustment unit adjusts the center-of-gravity movement distance threshold and sets the adjusted center-of-gravity movement distance threshold in the center-of-gravity movement distance threshold determination unit in the case the movable bedboard information that has been inputted to the movable bedboard information recognition unit has been adjusted.

In the case of the third to fifth aspects, the center-of-gravity position movement distance threshold is, e.g., set based on the movement distance when the user sits up and the user is a sitting-up state.

In the first to fifth aspects, the bed section has, e.g., a configuration in which the bedboard of the back portion of the bed section is capable of pivoting about the bedboard main body. The movable bedboard information is a back-raised angle of the movable bedboard. Preferably, the bed apparatus has alarm unit for generating an alarm when the state of the user has been detected.

In accordance with the present invention, the combined information of the body weight information and center-of-gravity position information of the user is determined, whereby the movement of the user can be more accurately monitored. Misdetections and reduction of detection accuracy can be prevented because the monitored area or the center-of-gravity movement distance threshold is suitably adjusted and set even when the movable bedboard moves and the center-of-gravity position of the bed user varies. The reliability of the system is thereby improved.

BRIEF DESCRIPTION OF THE DRAWINGS

FIG. 6 is a diagram showing the flow of sit-up detection of the bed apparatus according to the third embodiment of the present invention.

DESCRIPTION OF THE PREFERRED EMBODIMENTS

Figure 1:
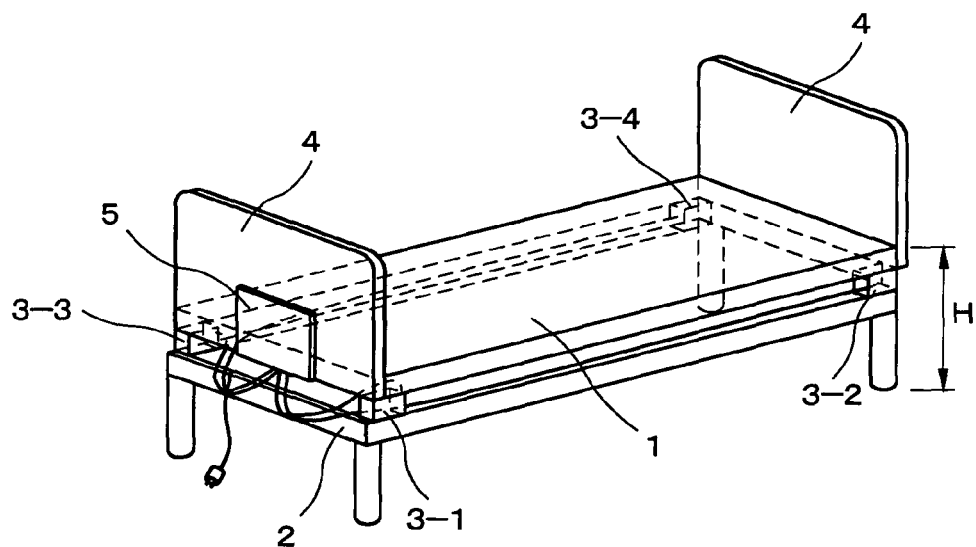
FIG. 1 is a schematic view of the bed apparatus according to embodiment 1 of the present invention.
Figure 2:
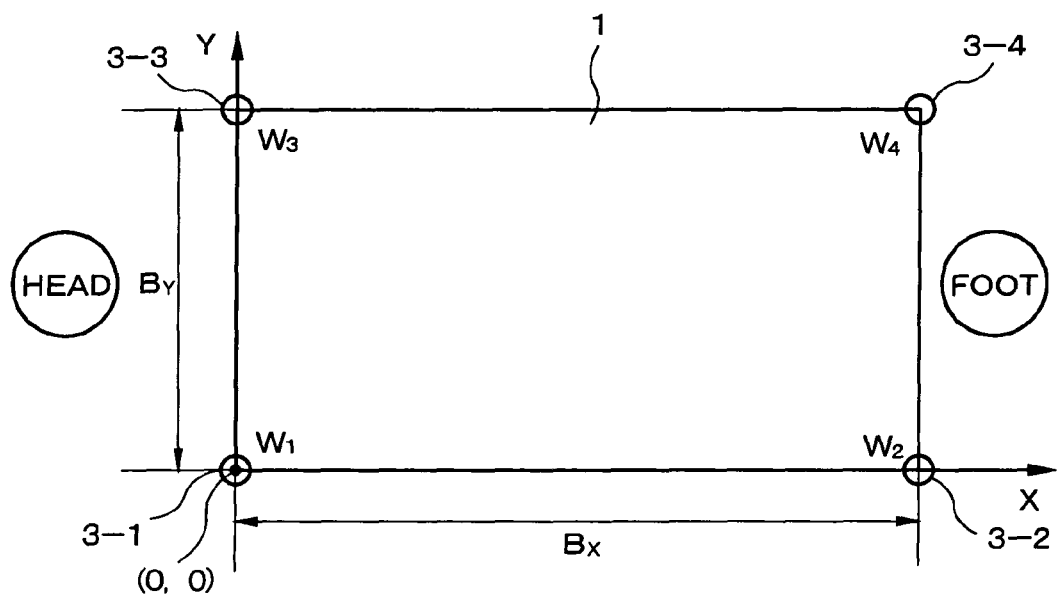
FIG. 2 is a schematic diagram showing an example in which four load sensors 3-1 to 3-4 are disposed at the four ends of the bed section 1.
Figure 3:
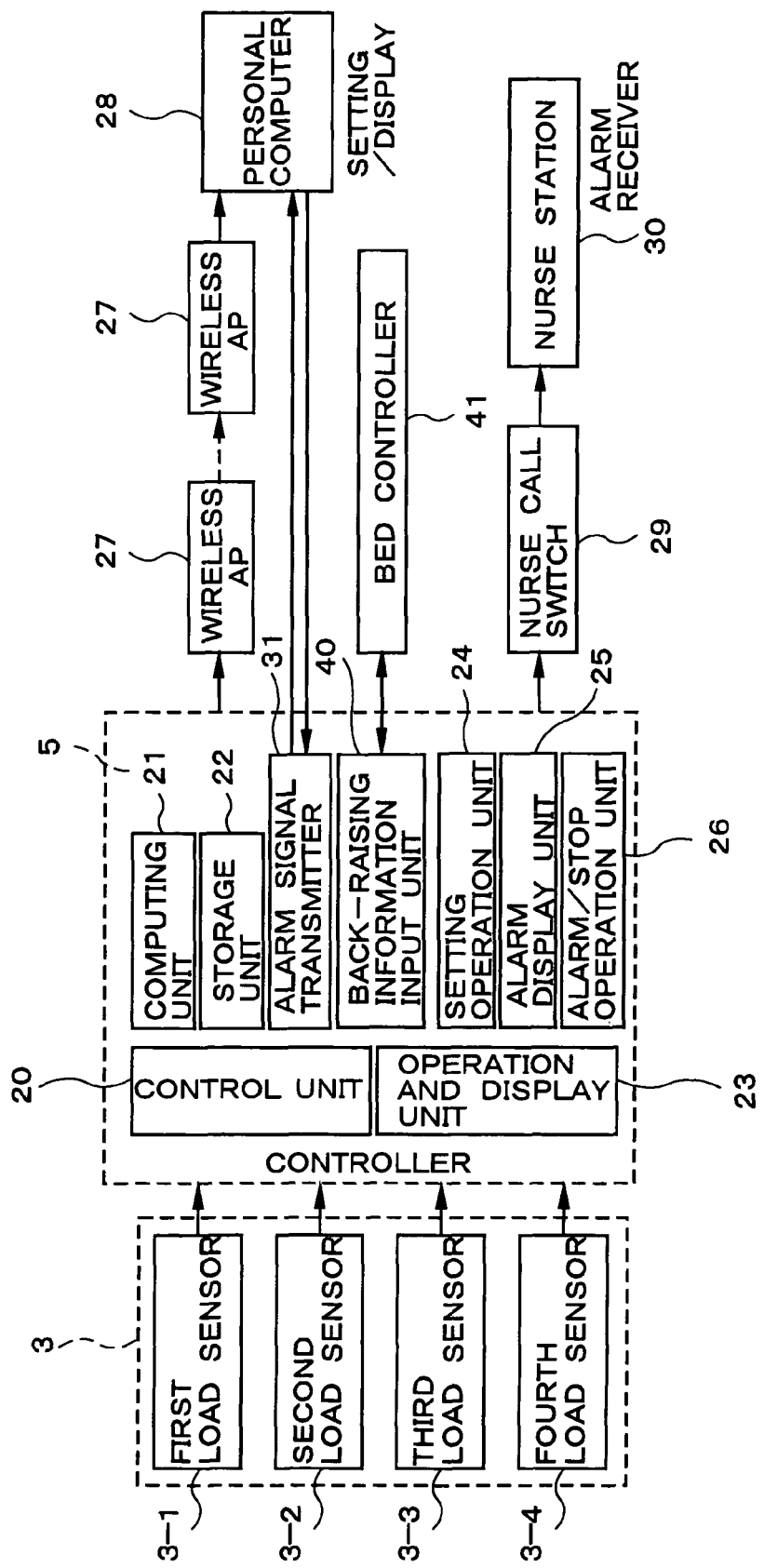
FIG. 3 shows a block diagram of when signals of the load sensors 3 are processed as information by the controller 5 and the functions are operated.

The bed apparatus according to embodiments of the present invention is described in detail below with reference to the attached diagrams. The bed apparatus of embodiment 1 provided with an abnormal position detection function will be described first. The abnormal position detection function is a function that detects that a patient (user) on a bed is positioned at the edge of the bed or is otherwise in an unnatural position on the bed for a prescribed length of time or longer. FIG. 1 is a schematic view of the bed apparatus according to embodiment 1 of the present invention. FIG. 2 is a schematic diagram showing an example in which four load sensors 3-1 to 3-4 are disposed at the four ends of a bed section 1. FIG. 3 shows a block diagram of when signals of load sensors 3 are processed as information and the functions are operated. Four load sensors 3 (3-1, 3-2, 3-3, and 3-4) for detecting the load on the bed section 1 and generating load signals are provided to the four corners (one to each corner) of the legged frame 2 that supports the bed section 1, as shown in FIG. 1. The load signals generated by the load sensors 3 are read at prescribed time intervals by a bed-departure prediction and detection system controller 5 (hereinafter referred to as "controller 5") provided to one of the wall sections 4 that are disposed on the two short sides of the bed section 1.

The controller 5 is provided with a body weight computing unit, a center-of-gravity position computing unit, a body weight threshold determination unit, a center-of-gravity position area determination unit, a body weight center-of-gravity position monitoring unit, a movable bedboard information recognition unit, a monitored area adjustment unit, a body weight threshold setting unit, a center-of-gravity position monitored area setting unit, a storage unit, an alarm apparatus, an alarm selection unit, and the like. Detection performed by each unit is carried out by software. The controller 5 reads load signals generated by the load sensors 3 at fixed time intervals. The body weight computing unit computes the body weight of the user on the bed section 1 on the basis of the signal thus read. Since a mattress, bed cover, railing, and other accessory items (not shown) are provided to the bed section 1, the body weight computing unit uses this state as a reference point (=0 kg, origin correction of the center-of-gravity position), reads the load signals of the bed section 1 using the controller 5 when the user is lying on the bed section 1, and computes the body weight $W_T$ of the user by computing the load increase from the reference point.

The center-of-gravity position computing unit computes the center-of-gravity position of the user on the bed section 1 on the basis of the load signals generated by the load sensors 3 that are read by the controller 5 at fixed intervals. As shown in FIG. 2, the head side is the side that connects the first load sensor 3-1 and the third load sensor 3-3, and the foot side is the side that connects the second load sensor 3-2 and the fourth load sensor 3-4. The origin (0, 0) is the left end of the head side (lower left end section of the bed section 1 in FIG. 2) of the bed section 1, $B_X$ is the distance between the first load sensor 3-1 and the second load sensor 3-2, and $B_Y$ is the distance between the first load sensor 3-1 and the third load sensor 3-3. The center-of-gravity position (X, Y) of the user can be expressed by the following formula 1, wherein $W_1$ to $W_4$ ($W_1+W_2+W_3+W_4=W_T$) are the calculated values of the load increase from the reference values of the load signals generated by the first to fourth load sensors 3-1 to 3-4 when the user is lying on the bed section 1. In accordance with this formula, the center-of-gravity position computing unit computes the center-of-gravity position of the user on the bed section 1.

$$(X, Y) = \left( \frac{(W_2 + W_4) \cdot B_X}{W_T}, \frac{(W_3 + W_4) \cdot B_Y}{W_T} \right) \quad \text{[EQ. 1]}$$

Figure 5:
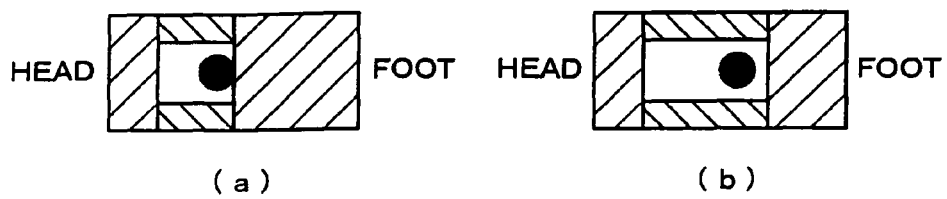
FIG. 5 is a diagram showing an example of the abnormal position area of the bed section 1.

The body weight threshold determination unit monitors the body weight $W_T$ of the user on the bed section 1 computed by the body weight computing unit, and determines whether the body weight $W_T$ of the user is equal to or greater than a prescribed body weight threshold $W_{T1}$. In other words, when the bed user is sitting at the edge of the bed with feet on the floor, the body weight detection value is less than the body weight of the user and is less than the body weight threshold $W_{T1}$. In this manner, when the user is sitting on the edge of the bed, such a state cannot be said to be dangerous or abnormal. The center-of-gravity position area determination unit monitors the center-of-gravity position $(X_1, Y_1)$ of the user and determines whether the center-of-gravity position $(X_1, Y_1)$ of the user is in the center-of-gravity position monitoring area of the bed section 1. The center-of-gravity position monitoring area includes the edges of the bed, i.e., side-sitting positions, as shown by the hatching in FIG. 5, and the presence of the bed user in the monitored area is thought to be unnatural or dangerous. Therefore, the center-of-gravity position monitored area may be all four edges surrounding the bed, or may be an area of a portion of the edges. Also, the center-of-gravity position monitored area is not necessarily limited to the side of the bed, and the monitored area is set depending on the objective of monitoring the abnormal state of the patient. When the bed user is lying recumbent on the bed and the body weight of the user is mostly set on the bed, the center-of-gravity position of the bed user on the edge of the bed is one in which the bed user tends to fall from the bed, and such a state is a dangerous or abnormal state.

The body weight threshold setting unit sets the body weight threshold $W_{T1}$ when it is determined whether the user on the bed section 1 is positioned on the bed. The center-of-gravity position monitored area setting unit sets the initial value of the monitored area of the center-of-gravity position. The body weight threshold $W_{T1}$ and the initial value of the monitored area are inputted from a personal computer connected to the controller 5, are computed in the computing unit of the controller 5, and are stored in the storage unit.

The alarm apparatus generates an alarm in accordance with the determination results of the body weight threshold determination unit and the center-of-gravity position area determination unit. The alarm selection unit has a function for selecting the existence and type of alarm.

FIG. 3 shows a block diagram of when signals of the first load sensor 3-1 to fourth load sensor 3-4 are processed as information by the controller 5 and the functions are operated. The load signals generated by the first to fourth load sensors 3-1 to 3-4 are read and computed by the computing unit 21 of the encoder 5 at fixed intervals. The computing unit 21 has a body weight computing unit for computing the body weight $W_T$ of a user on the bed section 1, a center-of-gravity position computing unit for computing the center-of-gravity position of the user on the bed section 1, a body weight threshold determination unit for determining whether the body weight of the user is equal to or greater than a prescribed body weight threshold $W_{T1}$, a center-of-gravity position area determination unit for monitoring the center-of-gravity position $(X_1, Y_1)$ of the user and determines whether the center-of-gravity position $(X_1, Y_1)$ of the user is in the center-of-gravity position monitored area of the bed section 1, a body weight center-of-gravity position monitoring unit for monitoring the time in which the body weight is at a prescribed threshold or higher and the center-of-gravity position is in a monitored area on the basis of the determination results of each determination unit, a movable bedboard information recognition unit for inputting the state of the movable bedboard of the bed section and recognizing the state of the movable bedboard, a monitored area adjustment unit for adjusting the center-of-gravity position monitored area on the basis of the movable bedboard information, a body weight threshold setting unit for setting the body weight threshold, a center-of-gravity position monitored area setting unit for setting the initial value of the center-of-gravity position monitored area, a storage unit, an alarm apparatus, an alarm selection unit, and other components; and also has a storage unit 22 for storing the body weight threshold, the center-of-gravity position monitored area, and the like that are used for making determinations, and an alarm signal generator 31 for generating an alarm by using the determination result of each determination unit. The controller 5 has an operation switch, a setting and operation unit 24 such as a power switch, an alarm display unit 25, a nurse call switch 29, and other alarm/stop operation units 26.

In the present embodiment, the movable bedboard information that shows the state of the movable bedboard is inputted from a bed controller 41 to an input unit 40. A so-called gatch bed has a back bedboard (back bottom), a hip bedboard (hip bottom), a knee bedboard (knee bottom), and a foot bedboard (foot bottom) that are mounted in the stated sequence on a horizontally disposed frame. The back bottom pivots about the end section of the hip bottom side, and the knee bottom is configured to pivot about the end section of the hip bottom side. The hip bottom is fixed to the frame, the foot bottom is connected to the knee bottom, and the connection point with the knee bottom is lifted as the knee bottom elevates, and is thereby elevated in coordination with the knee bottom. The back bottom thereby elevates so that the user's back elevates, and the knee bottom and foot bottom elevate so that the knees and feet can form an angular mound. Examples of gatch beds include those in which only the back bottom elevates and those in which the knee bottom also elevates. In either case, the back angle, the knee angle, and other states of the movable bedboard are inputted from the bed controller 41 to the gatch information input unit 40. The movable bedboard information recognition unit of the computing unit 21 recognized the state of the movable bedboard from the bedboard information inputted to the gatch information input unit 40, and recognizes the angle of the back bottom, the angle of the knee bottom, and other states. The monitored area adjustment unit of the computing unit 21 adjusts the monitored area in accordance with a prescribed reference by using the angle of the back bottom and/or the angle of the knee bottom. The information is set in the body weight center-of-gravity position monitoring unit, and updates the monitored area of the body weight center-of-gravity position monitoring unit on an ongoing basis.

The center of gravity is positioned slightly to the head side from the center of the bed if the bed user is facing upward in the center of the lengthwise direction of the bed when the bed is in a horizontal state, as shown in FIG. 5A. For this reason, the monitored area (abnormal position detection area) is the two edge portions of the bed, the relatively narrow end portions of the head side, and the relatively wide end portion of the foot side (substantially half of the foot side of the bed). However, the center-of-gravity position moves to the foot side in the manner shown in FIG. 5B when the back bottom elevates and the upper body of the bed user rises. For this reason, the monitored area adjustment unit moves the monitored area to the foot side. A linear actuator that is ordinarily used in the back-raising mechanism of a bed can ascertain the stroke distance thereof by using a potentiometer. A correlation is made between the stroke distance that corresponds to the back-raised angle and the change in the center-of-gravity position brought about by the change in the back-raised angle, whereby the abnormal position detection area that corresponds to the back-raised posture can be updated. It is also possible to store the center-of-gravity position prior to the back-raising operation and after the back-raising operation of the bed, and update the abnormal position detection area on the basis of the movement distance of the back-raising operation. The present embodiment is one in which the movable bedboard information is inputted from the bed controller 41 to the input unit 40, but no limitation is imposed thereby, and a caregiver or other staff may input the back-raising angle or other movable bedboard information via a personal computer, or the movable bedboard information may be input by operating a switch or the like.

An alarm apparatus generates an alarm signal via the controller 5, and a nurse station 30 can be notified via the nurse call switch (or signal) 29, or a remote personal computer 28 may be notified by relay through a LAN (Local Area Network) access point 27 by using a communication connector 12 when a plurality of beds are being managed.

Next, the operation of the abnormal position detection system according to embodiment 1 of the present invention configured in the manner described above will be described. Since a mattress, bed cover, railing, and other accessory items (not shown) are provided to the bed section 1, the body weight computing unit uses this state as a reference point (=0 kg, origin correction of the center-of-gravity position), reads the load signals of the bed section 1 using the controller 5 when the user is lying on the bed section 1, and computes the body weight $W_T$ of the user by computing the load increase from the reference point. An operation switch of the controller 5 (not shown) is pressed or a personal computer is operated immediately after the user has lain on the bed section 1, whereby the body weight of the user can be stored in the storage unit 22 of the controller 5. The body weight of the user at this time is set as the reference body weight $W_S$. The reference body weight $W_S$ of the user can also be stored in the storage unit of the controller 5 by inputting the body weight of the user that has been obtained using a weight scale or the like, and inputting the result via a personal computer connected to the controller 5.

Figure 4:
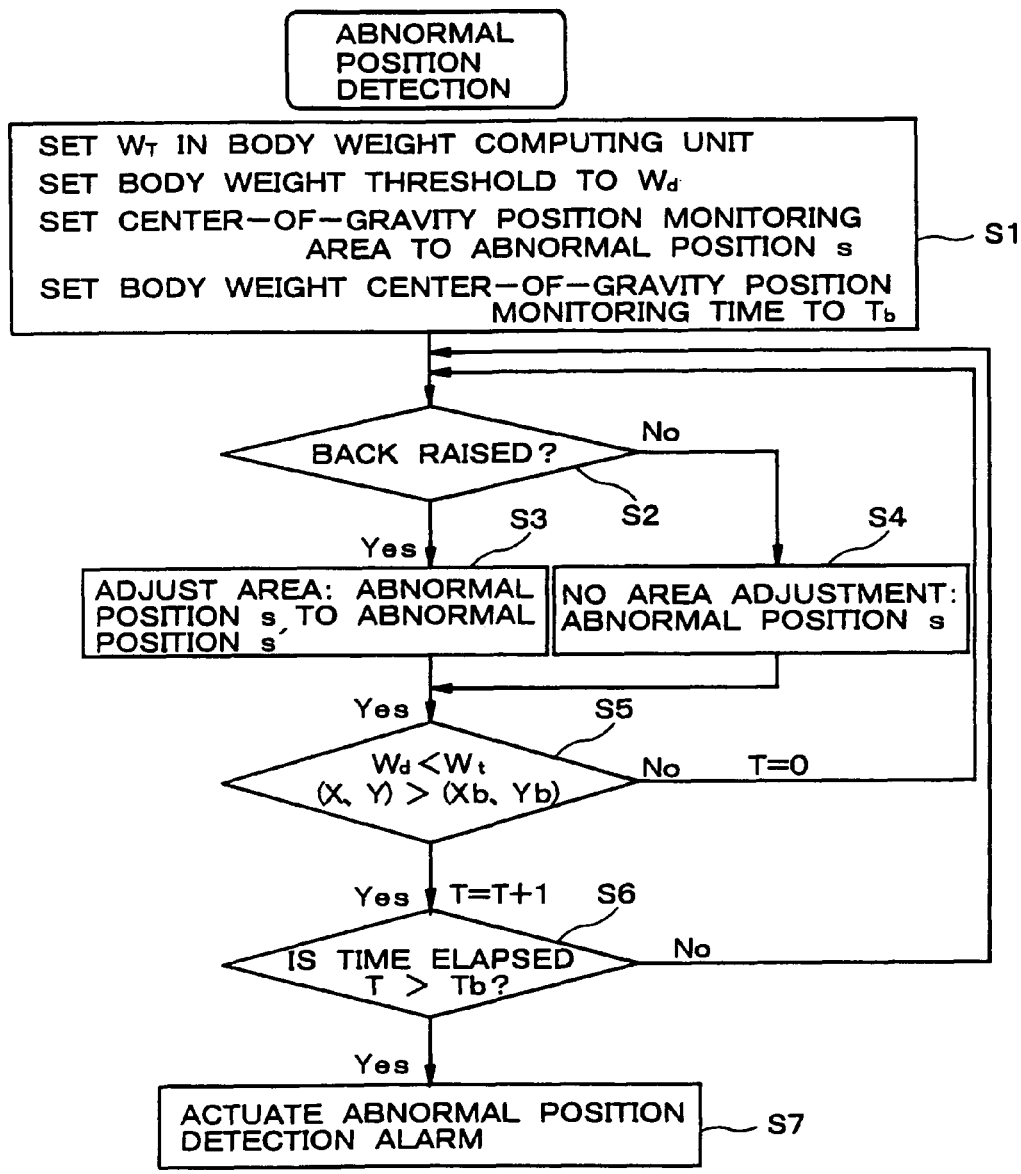
FIG. 4 is a diagram showing the flow of abnormal position detection of embodiment 1.

FIG. 4 is a flowchart showing the flow of abnormal position detection of embodiment 1. The reference body weight Wt of the user on the bed section 1 is computed by the body weight computing unit of the computing unit 21 of the controller 5 in advance when a reference is obtained, the body weight threshold Wd is set by the body weight threshold setting unit, the abnormal position (dangerous position) detection area (monitored area) is set by the center-of-gravity position monitored area setting unit, a monitoring time Tb for monitoring that the body weight is at a prescribed threshold or higher and that the center-of-gravity position is in the monitored area is set in the body weight center-of-gravity position monitoring unit, and these values are stored in the storage unit 22 of the controller 5 (step S1).

The movable bedboard information recognition unit determines at fixed time intervals whether a back-raising operation or another operation has been carried out (step S2). The monitored area adjustment unit adjusts the monitored area (abnormal position s) when a back-raising operation has been carried out, and this adjustment is set in the center of the gravity position area determination unit (step S3). The monitored area is not adjusted when the movable bedboard information recognition unit has not determined that a back-raising operation has been carried out (step S4).

In step S5, when the body weight threshold determination unit has determined that the body weight Wt is equal to or greater than the body weight threshold Wd at the initial determination timing (T=0), and the center-of-gravity position area determination unit has determined that the center-of-gravity position is within the monitored area, the process advances to step S6, this state is checked at fixed time intervals, and the elapsed time in which the state has continued is measured. When this state has continued for a fixed length of time Tb, an abnormal position detection alarm is actuated (step S7). On the other hand, in step S5 (at T=0), in the case that the body weight Wt has not been determined by the body weight threshold determination unit to be equal to or greater than the body weight threshold Wd, or in the case that the center-of-gravity position has not been determined by the center-of-gravity position area determination unit to be within the monitored area, or in both these cases, the process returns to step S2 when the body weight Wt or the center-of-gravity position no longer fits the conditions before the fixed time Tb elapses, even when the body weight Wt has, for a time, been determined to be equal to or greater than the body weight threshold Wd and the center-of-gravity position has been determined to be within the monitored area.

The existence of bedboard movement (existence of back-raising), and the body weight and center-of-gravity position are repeatedly determined at a fixed control timing, and an alarm is actuated when a state has continued for time Tb or longer in which the body weight Wt is equal to or greater than a body weight threshold Wd and the center-of-gravity position is within the monitored area.

In this manner, in the present embodiment, it can be detected with high accuracy and no misdetections whether the bed user is in an abnormal position on the bed, regardless of the movement of the bedboard, because it is determined whether or not the bed user is in an abnormal position on the bed by sampling the weight, and because the abnormal position that is to be determined is corrected with consideration given to back-raising operations, and other states of the movable bedboard.

The alarm apparatus has a function for generating an alarm depending on the result of detecting the side-sitting position, and the alarm selection unit has a function for selecting the existence of an alarm and the type of alarm. When an alarm is being generated, a nurse is notified by way of a nurse call switch 29, or a personal computer 28 or the like, and notification can be made using an alarm display unit 25 of the controller 5.

Embodiment 2 of the present invention will be described next. The present embodiment is one in which a body weight range determination unit that determines whether the body weight is within a prescribed range is provided in place of the body weight threshold determination unit in embodiment 1. Specifically, it is presumed that the body weight measurement value is within a prescribed range, rather than presuming that the body weight measurement value is at or above the body weight threshold Wd when the bed user is detected to be in an abnormal position.

In this manner, in the present embodiment, when the body weight measurement value is determined to be within a prescribed range and the center-of-gravity position is determined to be in an abnormal position, the bed user is detected to be in an abnormal position when such a state has continued for a fixed time Tb or longer. This causes the result of computing the center-of-gravity position to no longer indicate the position of the bed user and causes a misdetection to occur when a caregiver or the like places an object on the bed. However, when an upper limit is provided to the body weight detection value in the manner of embodiment 2, the bed user is not detected to be in an abnormal position even if the center-of-gravity position is inside the monitored area because the body weight detection value exceeds the upper limit when an object has been placed on the bed. Misdetections can thereby be avoided.

A bed apparatus according to embodiment 3 of the present invention will be described below. The present embodiment does not detect whether the position of the bed user is abnormal, as in the bed apparatuses in Embodiment 1 and Embodiment 2, but relates to a bed apparatus that has a function for detecting a sit-up movement of the bed user. Therefore, the present embodiment differs in that the controller 5 has a sit-up detection function, rather than an abnormal position detection function. The present embodiment is otherwise the same as the previous embodiments. The sit-up detection function detects that the user is in a state of making a sit-up movement.

The controller 5 of the bed apparatus of the present embodiment has a center-of-gravity movement distance computing unit, a center-of-gravity movement distance threshold determination unit, a center-of-gravity distance time difference setting unit, and a body weight range setting unit, in addition to the function of the controller 5 of the bed apparatus in embodiment 1.

The center-of-gravity position movement distance computing unit calculates the movement distance of the center-of-gravity position, based on the calculation results of the current position of the center of gravity and the calculation results of the center-of-gravity position at a previous point in time that precedes this time by a center-of-gravity movement distance time difference $T_2$ set by the center-of-gravity movement distance time difference setting unit, and this calculation is carried out each time the computing unit 21 of the controller 5 reads a load signal at each fixed interval of time. The movement that occurs when a user sits up is assumed to be a movement from a face-up position to a sitting position with the legs extended, or from a face-up position to a recumbent position, and then to a sitting position with the legs extended. In any of these movements, the center of gravity moves from the head side to the foot side in the length direction of the bed. Therefore, consideration is given to the center-of-gravity position movement distance in only the X axis direction during sit-up detection.

The movement distance $\Delta X$ of the center-of-gravity position in the X-axis direction can be expressed in EQ. 2 below, wherein $(X_2, Y_2)$ is the center-of-gravity position of the user at a time $t_2$, and $(X_{2-T2}, Y_{2-T2})$ is the center-of-gravity position of the past value $t_{2-T2}$ that precedes time $t_2$ by a center-of-gravity distance time difference $T_2$. According to this equation, the center-of-gravity movement distance computing unit calculates the movement distance $\Delta X$ of the center-of-gravity position of the user on the bed section 1. In the case that sit-up detection is used, the $\Delta X$ has directivity because the center of gravity moves from the head side to the foot side. This is opposite in a movement made when the user lies down. When $\Delta X$ is a positive value, for example, it can be determined that the user is sitting up; and when the value is negative, it can be determined that the user is lying down.

$$\Delta X = X_2 - X_{2-T2} (T_2\text{: movement distance of the center-of-gravity position at time difference}) \qquad [\text{EQ. 2}]$$

The body weight threshold unit monitors a body weight $W_T$ of the user on the bed section 1, which is calculated by the body weight computing unit; determines whether the body weight $W_T$ of the user at time $t_2$ is equal to or less than a first threshold; and determines whether the body weight $W_T$ of the user is within a prescribed range at time $t_2$–$T_2$ that precedes time $t_2$ by a center-of-gravity distance time difference $T_2$. The center-of-gravity movement distance threshold determination unit also monitors the movement distance $|\Delta X|$ of the center-of-gravity position of the user in the X axis direction, and determines whether the movement distance $|\Delta X|$ of the center-of-gravity position in the X axis direction of the user on the bed section 1 at time difference $T_2$ exceeds the center-of-gravity movement threshold.

The body weight threshold setting unit sets a body weight threshold for the body weight $W_T$ of the user when the user on the bed section 1 is determined to have made a sit-up movement. The body weight range setting unit sets a prescribed range for the body weight $W_T$. The center-of-gravity movement distance threshold setting unit sets the center-of-gravity movement distance threshold of the center-of-gravity position movement distance in the sit-up detection. The center-of-gravity movement distance time difference setting unit sets the center-of-gravity movement distance time difference $T_2$. These set values are inputted from a personal computer connected to the controller 5, are calculated in the computing unit of the controller 5, and are stored in a storage unit.

The alarm apparatus generates an alarm according to the determination results of the body weight threshold determination unit and the center-of-gravity movement distance determination unit. The alarm selection unit has a function for selecting the existence of an alarm and the type of alarm. When an alarm is generated, a nurse is notified by way of a nurse call switch 29, or a personal computer 28 or the like, and notification can be made using an alarm display unit 25 of the controller 5.

FIG. 6 shows the flow from sit-up detection until the alarm apparatus is activated. A reference body weight Ws of the user on the bed section 1 is calculated in advance at a reference time by the body weight computing unit of the computing unit 21 of the controller 5, a body weight threshold $W_{T2}$ is set by the body weight threshold setting unit, a prescribed body weight range $|W_{T2-1A}, W_{T2-1B}|$ is set by the body weight range setting unit, a center-of-gravity movement distance threshold $X_2$ is set by the center-of-gravity movement distance threshold setting unit, and the center-of-gravity movement distance time difference $T_2$ is set by the center-of-gravity movement distance time difference setting unit. These values are stored in the storage unit 22 of the controller 5 (step S11).

Next, the movable bedboard information recognition unit determines whether a back-raising operation has been carried out at a fixed control timing (Step S12). When the state of the moveable bedboard has been modified, a threshold adjustment unit adjusts the center-of-gravity movement distance threshold, and the adjusted center-of-gravity movement distance threshold is set by the center-of-gravity movement distance threshold determination unit (Step S13). When the state of the moveable bedboard has not been adjusted, the center-of-gravity movement distance threshold is not adjusted (Step S14). The movement distance of the center of gravity when a back-raising operation has been carried out has different values when the bed is in a horizontal state and the user sits up from a recumbent position, and when the bed user sits up in a state in which the bed back bottom is raised. Specifically, the latter is a shorter distance. In view of this situation, when the moveable bedboard (back bottom) is inclined (raised) rather than horizontal, the center-of-gravity movement threshold used to determine whether the bed user has sat up must be reduced. A linear actuator that is ordinarily used in the back-raising mechanism of a bed can ascertain the stroke distance thereof by using a potentiometer. A correlation is made between the stroke distance that corresponds to the back-raised posture (back-raised angle) and the change in the center-of-gravity position brought about by the change in the back-raised posture (back-raised angle), whereby the center-of-gravity movement distance threshold can be updated in accordance with the back-raised posture (back-raised angle). When the bed is in a horizontal state, the center-of-gravity movement distance threshold when the back-raised angle is a can also be calculated by the following equation: (Reference threshold)×cos(a), wherein the reference threshold is the center-of-gravity movement distance threshold for detecting a sit-up action, and a is the back-raised angle.

Next, the center-of-gravity movement distance threshold determination unit detects that the user has sat up (Step S15). When the user sits up, the center-of-gravity position moves in the longitudinal direction (X direction) of the bed. The center-of-gravity position movement distance $|\Delta X|$ of the user is calculated from the calculation results of present center-of-gravity position and from the calculation results of the center-of-gravity position at a previous point in time that precedes the present by a center-of-gravity movement distance time difference $T_2$ (e.g., five seconds), and this calculation is carried out each time the computing unit 21 of the controller 5 reads a load signal at each fixed interval of time. The movement distance $|\Delta X|$ of the center-of-gravity position is calculated from the calculation results of the center-of-gravity position of the user in the X axis direction at time $t_2$ and from the calculation results of the center-of-gravity position at point of time $t_{2-T2}$ that precedes time $t_2$ by a center-of-gravity movement distance time difference $T_2$ (e.g., 5 seconds) (the movement distance of the center-of-gravity position in the X axis direction at time difference $T_2$ (e.g., 5 seconds)). In the case that the movement distance $|\Delta X|$ of the center-of-gravity position is greater than a center-of-gravity movement threshold $X_2$ (e.g., $X_2$=30 cm), which is a second threshold (i.e., $|\Delta X|>X_2$), the second determination unit determines that the movement distance $|\Delta X|$ of the center-of-gravity position exceeds the center-of-gravity movement distance threshold $X_2$.

However, when only the center-of-gravity position movement distance in the X axis direction is monitored, the movement cannot be determined to be movement of the center of gravity that is caused by an item being placed on the bed section 1 in which the user is lying down, or another non-user person leaning or sitting on the bed section, and there are conceivably cases when these movements may be mistakenly determined to be a sit-up movement. In order to avoid such errors, the center-of-gravity movement distance threshold determination unit determines that the movement distance $|\Delta X|$ of the center-of-gravity position in the X axis direction exceeds the center-of-gravity movement distance threshold at time difference $T_2$. At the time that the center-of-gravity movement distance threshold determination unit makes this determination ($t=t_2$), the body weight threshold determination unit determines whether the body weight $W_T$ of the user on the bed section 1 is equal to or less than a first threshold ($W_T \leq W_{T2}$; e.g., 125% or less of a reference body weight $W_s$ of the user; in other words, whether the body weight $W_T$ is a load due to only the body weight of the user). Alternatively, the body weight range determination unit determines whether the body weight $W_T$ of the user is within a prescribed range ($W_{T2-1A} \leq W_T \leq W_{T2-1B}$; e.g., 75 to 125% of the reference body weight $W_s$ of the user; in other words, whether the user is present on the bed) during the point in time ($t=t_{2-T2}$) that precedes $t=t_2$ by a time difference $T_2$ (Step S16).

The user is detected as being in a state of sitting up when the center-of-gravity movement distance threshold determination unit has determined that the movement distance |ΔX| of the center-of-gravity position, which is calculated from the calculation results of the center-of-gravity position of the user in the X axis direction at time $t_2$ and from the calculation results of the center-of-gravity position at a point in time $t_{2-T2}$ that precedes time $t_2$ by a center-of-gravity movement distance time difference $T_2$, has exceeded the center-of-gravity movement distance threshold $X_2$, and has also determined that the body weight $W_T$ of the user at time $t_2$ is equal to or less than the body weight threshold $W_{T2}$, and that the body weight $W_T$ of the user is within a prescribed range (($W_{T2-1A} \leq W_T \leq W_{T2-1B}$ at a point in time $t_{2-T2}$ the precedes time $t_2$ by a center-of-gravity movement distance time difference $T_2$. An alarm can be generated in accordance with the result (step S17).

The alarm apparatus has a function for generating an alarm according to the sit-up detection results, and the alarm selection unit has a function for selecting the existence of an alarm and the type of alarm. When an alarm is generated, a nurse is notified by way of a nurse call switch 29, or a personal computer 28 or the like, and notification can be made using an alarm display unit 25 of the controller 5.

As described above, sit-up detection is carried out by determining whether the body weight $W_T$ of the user on the bed section 1 is equal to or less than a body weight threshold when the center-of-gravity position movement distance exceeds a center-of-gravity movement distance threshold, and/or determining whether the body weight $W_T$ of the user is within a prescribed range at a point in time that precedes by a time difference $T_2$ the time at which the center-of-gravity position movement distance exceeds the center-of-gravity movement distance threshold. As a result, it is possible to determine the movement to be movement of the center of gravity that is caused by an item being placed on the bed section 1 in which the user is lying down, or another non-user person leaning or sitting on the bed section, and errors in the sit-up detection can be reduced. The timing in which the body weight threshold determination unit determines whether the body weight measurement value is equal to or less than the body weight threshold can be set to occur when or after the center-of-gravity movement distance calculation unit calculates the movement distance of the center-of-gravity position and the resulting value exceeds the center-of-gravity movement distance threshold. Alternatively, the body weight threshold determination unit may determine whether the body weight measurement value is equal to or less than the body weight threshold at the point in time that precedes the point in time when the movement distance of the center-of-gravity position has exceeded the center-of-gravity movement distance threshold.

When the center of gravity moves due to the railing or other accessories being removed, and the center-of-gravity movement distance threshold determination unit has determined that the movement distance |ΔX| of the center-of-gravity position of the user at time difference $T_2$ has exceeded the center-of-gravity movement distance threshold $X_2$, the body weight range determination unit determines in conjunction therewith whether the body weight $W_t$ of the user is within a prescribed range at the point in time that precedes by a time difference $T_2$ the time at which the center-of-gravity position movement distance has exceeded a center-of-gravity movement distance threshold. Therefore, misdetections can be prevented.

Embodiment 4 of the present invention will be described next. The present embodiment is also used to detect a sit-up movement of a bed user. However, the present embodiment has a first body weight range determination unit for determining whether the body weight measurement value is within a first value range, and a second body weight range determination unit for determining whether the body weight measurement value is within a second value range. These units and the center-of-gravity movement distance threshold determination unit are used to detect the sit-up posture of the bed user. Specifically, a sit-up movement is detected when the first body weight range determination unit determines that the body weight measurement value is within a range of a first value range, the second body weight range determination unit determines that the body weight measurement value is within a range of a second value range, and the center-of-gravity movement distance threshold determination unit determines that the movement distance of the center-of-gravity position has exceeded a center-of-gravity movement distance threshold. In the present embodiment as well, the center-of-gravity movement distance threshold is adjusted when a back-raising movement occurs, or the state of the moveable bedboard is otherwise altered. Accordingly, the back-raising movement does not affect the detection, errors do not occur when the sit-up movement of the bed user is detected, and the sit-up movement can be detected with a high degree of accuracy.

In the present embodiment, a sit-up movement is detected when the center-of-gravity position movement distance has exceeded the center-of-gravity movement distance threshold, on the condition that the body weight measurement value is determined to be within a first value range before a sit-up movement, and the body weight measurement value is determined to be within a second value range after a sit-up movement. Specifically, when the center-of-gravity movement position is calculated, the center-of-gravity movement distance computing unit calculates the movement distance |ΔX| of the center-of-gravity position from the result of calculating the center-of-gravity position of the user in the X direction at a time $t_2$ and from the result of calculating the center of gravity at a point in time $t_2-T_2$ that precedes time $t_2$ by a center-of-gravity movement distance time difference $T_2$. A center-of-gravity movement essentially brought about by a sit-up movement is detected when the center-of-gravity movement distance determination unit has determined that the movement distance |ΔX| of the center-of-gravity position has exceeded the center-of-gravity movement distance threshold $X_2$ at time $t_2$. In view of this situation, a sit-up movement is detected when one of following determination results apply: the first body weight range determination unit determines whether the body weight measurement value is within a first value range at a time t2–T2 that precedes time $t_2$ by a center-of-gravity movement distance time difference T2; or the second body weight range determination unit determines whether the body weight measurement value is within a second value range at time t2. In the present embodiment, a sit-up movement is thereby detected when the center-of-gravity position movement distance of the user on the bed has exceeded the center-of-gravity movement distance threshold (due to a sit-up movement), the body weight measurement value when the center of gravity moves (when a sit-up movement begins) has been determined to fall within a first value range, and the body weight measurement value has been determined to fall within a second value range at the point in time when the center-of-gravity movement distance threshold is exceeded.

The user is determined to indeed be on the bed when the body weight measurement value prior to a sit-up movement falls within a first value range. Therefore, the first value range is set to a range that is close to the body weight of the user. The user is determined to be on the bed when the body weight measurement value falls within a second value range after the sit-up movement has occurred. Therefore, in order to prevent movements other than a sit-up movement from being detected as a sit-up movement, a sit-up movement is detected when the movement distance of the center-of-gravity position has exceeded the center-of-gravity movement distance threshold, on the condition that the body weight measurement value is determined to be within a first range when the center of gravity moves (when a sit-up movement begins) is determined to be within a first value range, and the body weight measurement value is determined to be within a second value range at the point in time when the center-of-gravity movement distance threshold is exceeded.

If there is a possibility that the bed user is on the bed after the sit-up movement, there is also the possibility that the user may bring his feet to the floor and sit on the side of the bed. The body weight measurement value is dramatically reduced when the user is in a side-sitting position and rests his feet on the floor. In order for this case to also be detected as a sit-up movement, a lower limit of the second value range must be set so as to be lower than the lower limit of the first value range.

There are also cases in which the center of gravity moves by a distance that is equal to or greater than the center-of-gravity movement distance threshold when, in an extreme example, the user quickly rises from the bed or jumps off of the bed, whereupon the weight on the bed rapidly decreases. Such cases are not actually a sit-up movement, but may be errantly detected as a sit-up movement. In this case, errant detection can be prevented by providing a lower limit in the same manner as in the second value range. When the bed user is in a side-sitting position and stands up from this position, the center of gravity is moved by moves due to the momentum created when the user stands completely erect. When there is no lower limit in the second value range, the body weight measurement value may fall within the first value range before the center of gravity moves, and this may be errantly detected as a standing movement. However, in this case as well, providing the second value range with a lower limit makes it possible to determine whether the movement is bed departure (bed departure from a side-sitting position) in which the body weight measurement value is zero, or a sit-up movement, and errant detections can be prevented.

An upper limit is provided in the first value range and second value range for the following reasons. Specifically, the center of gravity may move when an item is placed on the bed at the head side or foot side. Also, movement of the center of gravity caused by some type of disturbance may also be detected, even if a user is not on the bed. Therefore, if the body weight measurement value exceeds the upper limit even when a movement is detected in the center of gravity, it is determined that the movement of the center of gravity is not produced by a sit-up movement and must not to be detected as a sit-up movement.

In embodiments 1 through 4 above, the thresholds, prescribed ranges, side-sitting position, and the like are inputted using a personal computer connected to the controller 5, and these parameters are calculated by the computing unit 21 of the controller 5. However, the calculations may also be made by the personal computer, and the calculation results can be inputted to the controller 5 from the personal computer.

What is claimed is:

1. A bed apparatus having a movable bedboard, comprising:

load measuring unit for detecting the load of a bed section and generating a load signal;

body weight computing unit for computing the weight of a user positioned on the bed section on the basis of said load signal;

body weight threshold determination unit for determining whether said body weight is equal to or greater than a prescribed threshold;

center-of-gravity position computing unit for computing a center-of-gravity position of said user on the basis of said load signal;

center-of-gravity position area determination unit for determining whether said center-of-gravity position is in a monitored area of the bed section;

body weight center-of-gravity position monitoring unit for monitoring the time in which said body weight is equal to or greater than a prescribed threshold and said center-of-gravity position is in said monitored area, on the basis of the determination result of said body weight threshold determination unit and center-of-gravity position area determination unit;

movable bedboard information recognition unit for inputting a state of a movable bedboard of the bed; and monitored area adjustment unit for adjusting said monitored area on the basis of the movable bedboard information of said movable bedboard information recognition unit, wherein the state of said user is detected when said monitored area adjustment unit adjusts the monitored area and sets the adjusted monitored area in said center-of-gravity position area determination unit, and said center-of-gravity position monitoring unit detects the state of said user when the monitored time is continuous and has exceeded a prescribed time, in the case that the movable bedboard information that has been inputted to said movable bedboard information recognition unit has been adjusted.

2. A bed apparatus having a movable bedboard, comprising:

load measuring unit for detecting the load of a bed section and generating a load signal;

body weight computing unit for computing the weight of a user positioned on the bed section on the basis of said load signal;

body weight range determination unit for determining whether said body weight is within a prescribed body weight range;

center-of-gravity position computing unit for computing a center-of-gravity position of said user on the basis of said load signal;

center-of-gravity position area determination unit for determining whether said center-of-gravity position is in a monitored area of the bed section;

body weight center-of-gravity position monitoring unit for monitoring the time in which said body weight is within a prescribed range and said center-of-gravity position is in said monitored area, on the basis of the determination result of said body weight range determination unit and center-of-gravity position area determination unit;

movable bedboard information recognition unit for inputting a state of a movable bedboard of the bed; and monitored area adjustment unit for adjusting said monitored area on the basis of the movable bedboard information of said movable bedboard information recognition unit, wherein the state of said user is detected when said monitored area adjustment unit adjusts the monitored area and sets the adjusted monitored area in said center-of-gravity position area determination unit, and said center-of-gravity position monitoring unit detects the state of said user when the monitored time is continuous and has exceeded a prescribed time, in the case that the movable bedboard information that has been inputted to said movable bedboard information recognition unit has been adjusted.

3. The bed apparatus having a movable bedboard according to claim 1, wherein said monitored area is an abnormal position of the bed section and shows that the state of said user is an unnatural state or in an unnatural position.

4. The bed apparatus having a movable bedboard according to claim 2, wherein said monitored area is an abnormal position of the bed section and shows that the state of said user is an unnatural state or in an unnatural position.

5. A bed apparatus having a movable bedboard, comprising:
 load measuring unit for detecting the load of a bed section and generating a load signal;
 body weight computing unit for computing the weight of a user positioned on the bed section on the basis of said load signal;
 body weight threshold determination unit for determining whether said body weight is equal to or less than the body weight threshold;
 center-of-gravity position computing unit for computing a center-of-gravity position of said user on the basis of said load signal;
 center-of-gravity movement distance computing unit for computing, based on the computation result of said center-of-gravity position, the center-of-gravity movement distance of the center-of-gravity position;
 center-of-gravity movement distance threshold determination unit for determining whether the movement distance of said center-of-gravity position has exceeded a center-of-gravity movement distance threshold;
 movable bedboard information recognition unit for inputting the state of a movable bedboard of a bed; and
 threshold adjustment unit for adjusting said center-of-gravity movement distance threshold on the basis of the movable bedboard information of said movable bedboard information recognition unit, wherein
 the state of said user is detected when said threshold adjustment unit adjusts the center-of-gravity movement distance threshold and sets the adjusted center-of-gravity movement distance threshold in said center-of-gravity movement distance threshold determination unit, said center-of-gravity movement distance threshold determination unit determines that the movement distance of the center-of-gravity position has exceeded said center-of-gravity movement distance threshold, and said body weight threshold determination unit determines that said body weight is equal to or less than said body weight threshold, in the case that the movable bedboard information that has been inputted to said movable bedboard information recognition unit has been adjusted.

6. A bed apparatus having a movable bedboard, comprising:
 load measuring unit for detecting the load of a bed section and generating a load signal;
 body weight computing unit for computing the weight of a user positioned on the bed section on the basis of said load signal;
 body weight range determination unit for determining whether said body weight is within a prescribed range;
 center-of-gravity position computing unit for computing a center-of-gravity position of said user on the basis of said load signal;
 center-of-gravity movement distance computing unit for computing, based on the computation result of said center-of-gravity position, the center-of-gravity movement distance of the center-of-gravity position;
 center-of-gravity movement distance threshold determination unit for determining whether the movement distance of said center-of-gravity position has exceeded a center-of-gravity movement distance threshold;
 movable bedboard information recognition unit for inputting the state of a movable bedboard of a bed; and
 threshold adjustment unit for adjusting said center-of-gravity movement distance threshold on the basis of the movable bedboard information of said movable bedboard information recognition unit, wherein
 the state of said user is detected when said threshold adjustment unit adjusts the center-of-gravity movement distance threshold and sets the adjusted center-of-gravity movement distance threshold in said center-of-gravity movement distance threshold determination unit, said center-of-gravity movement distance threshold determination unit determines that the movement distance of the center-of-gravity position has exceeded said center-of-gravity movement distance threshold, and said body weight range determination unit determines that said body weight is within said prescribed range, in the case that the movable bedboard information that has been inputted to said movable bedboard information recognition unit has been adjusted.

7. A bed apparatus having a movable bedboard, comprising:
 load measuring unit for detecting the load of a bed section and generating a load signal;
 body weight computing unit for computing the weight of a user positioned on the bed section on the basis of said load signal;
 first body weight range determination unit for determining whether said body weight is within the range of a first value range;
 second body weight range determination unit for determining whether said body weight is within the range of a second value range;
 center-of-gravity position computing unit for computing a center-of-gravity position of said user on the basis of said load signal;
 center-of-gravity movement distance computing unit for computing, based on the computation result of said center-of-gravity position, the movement distance of the center-of-gravity position;
 center-of-gravity movement distance threshold determination unit for determining whether the movement distance of said center-of-gravity position has exceeded a center-of-gravity movement distance threshold;
 movable bedboard information recognition unit for inputting the state of a movable bedboard of a bed; and
 threshold adjustment unit for adjusting said center-of-gravity movement distance threshold on the basis of the movable bedboard information of said movable bedboard information recognition unit, wherein
 in a case in which the movable bedboard information that has been inputted to said movable bedboard information recognition unit has been adjusted, the state of said user is detected when said threshold adjustment unit adjusts the center-of-gravity movement distance threshold and sets the adjusted center-of-gravity movement distance threshold in said center-of-gravity movement distance threshold determination unit, and said center-of-gravity movement distance threshold determination unit determines that the movement distance of the center-of-gravity position has exceeded said center-of-gravity movement distance threshold, whereupon said first body weight range determination unit determines that said body weight is within the range of said first value range before the movement distance of said center-of-gravity position exceeds said center-of-gravity position movement distance threshold, and said second body weight range determination unit determines that said body weight is within the range of said second value range when the movement distance of said center-of-gravity position has exceeded said center-of-gravity position movement distance threshold or thereafter.

8. The bed apparatus having a movable bedboard according to claim 5, wherein said center-of-gravity position movement distance threshold is set based on the movement distance when said user is raised up, and said user is a raised state.

9. The bed apparatus having a movable bedboard according to claim 6, wherein said center-of-gravity position movement distance threshold is set based on the movement distance when said user is raised up, and said user is a raised state.

10. The bed apparatus having a movable bedboard according to claim 7, wherein said center-of-gravity position movement distance threshold is set based on the movement distance when said user is raised up, and said user is a raised state.

11. The bed apparatus having a movable bedboard according to claim 1, wherein said bed section is a movable bedboard in which the bedboard of the back section thereof is capable of pivoting with respect to the bedboard main body, and said movable bedboard information is a back-raised angle of said movable bedboard.

12. The bed apparatus having a movable bedboard according to claim 2, wherein said bed section is a movable bedboard in which the bedboard of the back section thereof is capable of pivoting with respect to the bedboard main body, and said movable bedboard information is a back-raised angle of said movable bedboard.

13. The bed apparatus having a movable bedboard according to claim 5, wherein said bed section is a movable bedboard in which the bedboard of the back section thereof is capable of pivoting with respect to the bedboard main body, and said movable bedboard information is a back-raised angle of said movable bedboard.

14. The bed apparatus having a movable bedboard according to claim 6, wherein said bed section is a movable bedboard in which the bedboard of the back section thereof is capable of pivoting with respect to the bedboard main body, and said movable bedboard information is a back-raised angle of said movable bedboard.

15. The bed apparatus having a movable bedboard according to claim 7, wherein said bed section is a movable bedboard in which the bedboard of the back section thereof is capable of pivoting with respect to the bedboard main body, and said movable bedboard information is a back-raised angle of said movable bedboard.

16. The bed apparatus having a movable bedboard according to claim 1, comprising alarm unit for generating an alarm when the state of said user has been detected.

17. The bed apparatus having a movable bedboard according to claim 2, comprising alarm unit for generating an alarm when the state of said user has been detected.

18. The bed apparatus having a movable bedboard according to claim 5, comprising alarm unit for generating an alarm when the state of said user has been detected.

19. The bed apparatus having a movable bedboard according to claim 6, comprising alarm unit for generating an alarm when the state of said user has been detected.

20. The bed apparatus having a movable bedboard according to claim 7, comprising alarm unit for generating an alarm when the state of said user has been detected.

* * * * *